United States Patent [19]

Jackisch

[11] Patent Number: 4,521,624

[45] Date of Patent: Jun. 4, 1985

[54] PROCESS FOR MAKING CYCLIC AMINES

[75] Inventor: Philip F. Jackisch, Baton Rouge, La.

[73] Assignee: Ethyl Corporation, Richmond, Va.

[21] Appl. No.: 601,032

[22] Filed: Apr. 16, 1984

[51] Int. Cl.³ .................. C07C 85/00; C07C 85/08
[52] U.S. Cl. .................................................. 564/446
[58] Field of Search ...................................... 564/446

[56] References Cited

U.S. PATENT DOCUMENTS

| 1,762,742 | 6/1930 | Reppe | 564/446 X |
| 3,415,881 | 12/1968 | Dunlop et al. | 564/446 |
| 3,535,379 | 10/1970 | Besson et al. | 564/446 |
| 3,994,975 | 11/1976 | Alink et al. | 564/446 |
| 4,152,353 | 5/1979 | Habermann | 564/446 X |
| 4,153,581 | 5/1979 | Habermann | 564/446 X |

Primary Examiner—Paul F. Shaver
Attorney, Agent, or Firm—Donald L. Johnson; John F. Sieberth; W. G. Montgomery

[57] ABSTRACT

Process for preparing cyclic amines by the reductive amination of saturated cyclic ketones. For example, cyclohexanone is reductively aminated to obtain N,N-dimethylcyclohexylamine.

17 Claims, No Drawings

PROCESS FOR MAKING CYCLIC AMINES

TECHNICAL FIELD

This invention relates to the reductive amination of saturated cyclic ketones to form cyclic amines.

U.S. Pat. No. 4,040,799 discloses a method for the reductive amination of unsaturated cyclic ketones by reacting unsaturated ketones with an amine in the presence of hydrogen and a hydrogenation catalyst such as palladium, platinum or nickel so as to not only saturate the double bond but also to convert the ketone group to an amino group.

THE INVENTION

In accordance with the present invention, a saturated cyclic ketone is converted to a cyclic amine by reacting an amine with the saturated ketone in the presence of hydrogen and a hydrogenation catalyst.

Any amine or substituted amine can be used in the process provided it has a >NH group and the remaining groups of the amine do not interfere with the reductive amination. Preferred amines, however, are those having no more than one hydrogen atom attached to the nitrogen atom and are represented by the structure:

wherein R is hydrogen or methyl and R' is alkyl, cyclohexyl, hydroxyalkyl and aminoalkyl.

The saturated cyclic ketones of the present invention are those having the following structure:

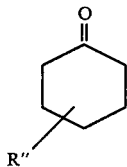

wherein R" is hydrogen or a substituted group such as alkyl, alkenyl, aryl, or alkaryl.

The process can be illustrated by the following reaction:

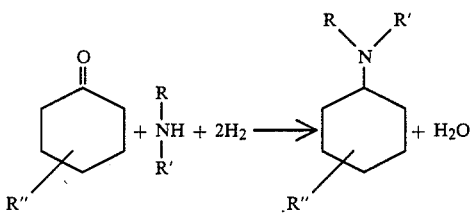

wherein R, R' and R" are as described above.

The reaction is carried out in the presence of a hydrogenation catalyst such as palladium, platinum or nickel. Palladium is preferred. The reaction should be carried out at a temperature ranging from about 70° to 135° C., although lower or higher temperatures ranging from ambient up to, but not including, the decomposition temperatures of the reactants or products can be used, if desired. The reaction is carried out at suitable elevated pressures, typically ranging from about 10–2000 psig for a period of time sufficient for the reaction to go to completion or substantially to completion.

In a highly preferred embodiment of the invention, the reductive amination process is carried out in the presence of water. It has been found that water in the reaction system exerts a yield enhancing effect on the amount of cyclic amine produced by the process. This is more fully illustrated in the examples set forth below. The amount of water present in the reaction system should range from at least 1.0% by weight to about 50% by weight based on the total weight of the reaction mass.

Thus, in a highly preferred embodiment of the invention, there is provided a process for the reductive amination of a saturated cyclic ketone which comprises reacting, in an aqueous medium, said saturated cyclic ketone with an amine in the presence of hydrogen and a hydrogenation catalyst whereby said saturated cyclic ketone is converted to the corresponding cyclic amine.

The compounds produced by the process of the invention are useful as fuel additives. More specifically, these additives act to inhibit or retard the deterioration of fuel oil during storage when added thereto. In general, only a minor amount of additive, sufficient to inhibit oil deterioration and the attendant formation of sludge, is added to the fuel.

The amount of additive employed generally should range from about 0.0001% to 0.1% based on the weight of the oil, although greater or lesser amounts can be used, if desired.

Fuel oils employing the stability additives produced by the present process are those hydrocarbon fractions having an initial boiling point of at least 100° F. and an end boiling point not higher than 750° F., and boiling substantially continuously throughout their distillation range. Such fuel oils are generally known as distillate fuel oils and can be straight-run distillate fuel oils, catalytically or thermally cracked distillate fuel oils or mixtures of straight-run distillates, naphthas and the like with cracked distillate stocks. They include Nos. 1, 2 and 3 fuel oils used in domestic heating and as diesel fuel oils.

The distillate fuel compositions containing the cyclic amine stabilizers of the present invention may also contain other additives, such as, corrosion inhibitors, metal deactivators, detergents, cold flow improvers, inert solvents or diluents, and the like.

The practice of this invention will become further apparent from the following illustrative examples.

EXAMPLE 1

Reductive Amination of Cyclohexanone with Palladium-on-Carbon

A 300 ml autoclave was charged with 62.94 g (0.6413 mole) of cyclohexanone, 72.27 g (0.6413 mole) of 40% dimethylamine in water, and 0.10 g of 5% palladium-on-carbon. The volume available for hydrogen in the autoclave was estimated to be 78 ml at 115° C. The autoclave was flushed three times with 60 psig of nitrogen. Stirring and heating were begun and when the temperature reached 72° C., the autoclave was pressured to 150 psig with hydrogen. The initial rate of hydrogen absorption at 68° C. was 70 psi/min. After 9 additional minutes of heating, the temperature was 115° C. and the rate of hydrogen absorption was 65 psi/min. Eighty minutes later, the rate of hydrogen absorption was less than 1 psi/min at 115° C. and the reaction was shut down.

The cooled autoclave was vented, opened, and its contents were poured out. The autoclave was rinsed with 44.93 g of absolute ethanol and this was added to the reaction mixture making the liquid phase homogeneous. The weight of recovered products was 133.98 g (98.1% of theory). The diluted reaction mixture was filtered through Whatman #1 paper to remove catalyst. Gas chromatography and mass spectroscopy confirmed that the major product was N,N-dimethylcyclohexylamine. Among the organic materials (not counting ethanol or dimethylamine), gas chromatography showed 96.30% N,N-dimethylcyclohexylamine, 2.38% cyclohexanol, 1.22% cyclohexanone, and 0.10% cycloheptanone. The conversion was 98.78% and N,N-dimethylcyclohexylamine made up 97.5% of the products.

Substantially as described in Example 1, several runs were made in which cyclohexanone was reacted with dimethylamine under reductive conditions. The results are summarized in the following table.

TABLE

Reductive Amination of Cyclohexanone

| Example No. | Catalyst 5% Pd/C g | Dimethyl- Amine (DMA) g | Cyclo- hexanone g | Reaction Pressure psig | Reaction Temp. °C. | Reaction Time (mins) | Con- version | Yield | N,N—DMCHA[1] | Cyclo- Hexanol | N,N—DMA[2] |
|---|---|---|---|---|---|---|---|---|---|---|---|
| 2 | 1.0 | 62.1 g of 40% DMA in H$_2$O | 52.52 | 50–150 | 90 | 36 | 99.4% | 98.0% | 97.39% | 0.77% | 1.2% |
| 3 | .27 | 80.0 g of 40% DMA in H$_2$O | 63.47 | 100–200 | 110 | 47 | 100.0% | 97.5% | 97.50% | 2.27% | 0% |
| 4 | .09 | 26.77 | 52.93 | 100 | 115 | 37 | 82.9% | 89.4% | 74.2% | 8.0% | 0.3% |
| 5 | .05 | 29.71 | 59.29 | 600 | 115 | 120 | 90.8% | 84.0% | 76.2% | 14.3% | 0% |
| 6 | .20 | 29.70 | 60.57 | 600 | 115 | 44 | 92.2% | 91.9% | 84.7% | 6.6% | 0.4% |
| 7 | .10 | 29.26 g + 5 g of H$_2$O | 60.80 | 600 | 115 | 123 | 100.0% | 92.0% | 92.0% | 6.8% | 1.1% |
| 8 | .30 | 69.9 g of 40% DMA in H$_2$O | 60.20 | 600 | 115 | 40 | 98.0% | 99.7% | 97.6% | 0% | 0% |
| 9 | .30 | 70.3 g of 40% DMA in H$_2$O | 60.05 | 600 | 115 | 60 | 99.7% | 95.3% | 97.2% | 3.1% | 0.1% |

[1]N,N—dimethylcyclohexylamine
[2]N,N—dimethylaniline

I claim:

1. A process for the reductive amination of a saturated cyclic ketone which comprises reacting said saturated ketone with an amine in the presence of hydrogen and a hydrogenation catalyst whereby said saturated cyclic ketone is converted to the corresponding cyclic amine.

2. The process of claim 1 wherein said amine has the structural formula:

wherein R is hydrogen or methyl and R' is alkyl, cyclohexyl, hydroxyalkyl and aminoalkyl.

3. The process of claim 2 wherein said amine is dimethylamine.

4. The process of claim 1 wherein said saturated ketone is cyclohexanone.

5. The process of claim 1 wherein the cyclic amine produced by the process is N,N-dimethylcyclohexylamine.

6. The process of claim 1 wherein said process is carried out at an elevated temperature ranging from about 70° to about 135° C.

7. The process of claim 1 wherein said process is carried out at an elevated pressure ranging from about 10 to 2000 psig.

8. The process of claim 1 wherein said hydrogenation catalyst is palladium.

9. The process of claim 1 wherein said reaction is carried out in the presence of water.

10. The process of claim 9 wherein the amount of water present in said reaction is from about 1.0% by weight to about 50% by weight based on the total weight of the reaction mass.

11. The process of claim 9 wherein said amine has the structural formula:

$$\begin{array}{c} R \\ / \\ N \\ \backslash \\ R' \end{array}$$

wherein R is hydrogen or methyl and R' is alkyl, cyclohexyl, hydroxyalkyl and aminoalkyl.

12. The process of claim 11 wherein said amine is dimethylamine.

13. The process of claim 9 wherein said saturated ketone is cyclohexanone.

14. The process of claim 9 wherein the cyclic amine produced by the process is N,N-dimethylcyclohexylamine.

15. The process of claim 9 wherein said process is carried out at an elevated temperature ranging from about 70° to about 135° C.

16. The process of claim 9 wherein said process is carried out at an elevated pressure ranging from about 10 to 2000 psig.

17. The process of claim 9 wherein said hydrogenation catalyst is palladium.

* * * * *